United States Patent [19]

Osaki et al.

[11] Patent Number: 5,046,356
[45] Date of Patent: Sep. 10, 1991

[54] APPARATUS FOR DETERMINING WATER CONTENT OF POWDER/GRANULE

[75] Inventors: Shigeyoshi Osaki, Takarazuka; Kiyokazu Sakai, Nishinomiya; Shinichi Nagata, Matsubara, all of Japan

[73] Assignee: Kanzaki Paper Manufacturing Co., Ltd., Tokyo, Japan

[21] Appl. No.: 413,323

[22] Filed: Sep. 27, 1989

[30] Foreign Application Priority Data

Sep. 28, 1988 [JP] Japan .............................. 63-126705[U]

[51] Int. Cl.$^5$ ............................................... G01N 5/02
[52] U.S. Cl. ........................................ 73/73; 324/640
[58] Field of Search .................... 73/73; 324/634, 640, 324/643

[56] References Cited

U.S. PATENT DOCUMENTS

| | | | |
|---|---|---|---|
| 3,360,721 | 12/1967 | Pullman | 324/640 |
| 4,211,970 | 7/1980 | Fitzky et al. | 324/634 |
| 4,485,284 | 11/1984 | Pakulis | 219/10.55 R |
| 4,716,360 | 12/1987 | Pakulis | 324/640 |

FOREIGN PATENT DOCUMENTS 257054 11/1987 Japan .
7319 2/1989 Japan .
9574 2/1989 Japan .

Primary Examiner—Thomas B. Will
Assistant Examiner—W. Morris Worth
Attorney, Agent, or Firm—Morgan & Finnegan

[57] ABSTRACT

An apparatus for determining water content of powder/granule sample including a rectangular waveguide system substantially set up in the upright or vertical disposition, consisting of a microwave transmitting converter, a microwave waveguide, and a microwave receiving converter; the apparatus comprising: a sample container for containing powder or granular sample and being accommodated inside of the microwave waveguide; the waveguide being provided with an inlet hole communicated to the inner space of the cavity resonator at one of side walls, and having a door for opening and closing the hole and a supporting element for the sample container within the waveguide; a buffer weighing system for supporting the hollow waveguide on a supporting table in the upright or vertical disposition and generates electric signals designating the supporting weight; and signal processing means for receiving signal output from the microwave receiving converter and the other signal from said buffer weighing system, storing and arithmetically processing these signals.

10 Claims, 2 Drawing Sheets

APPARATUS FOR DETERMINING WATER CONTENT OF POWDER/GRANULE

TECHNICAL FIELD

The present invention relates to an apparatus for determining water content of powder and granules by measuring attenuation in microwave transmitting through a sample.

BACKGROUND ART

Conventionally, there are a variety of methods for determining water content of powder and particles ground from wood chip available as the material of paper including the absolute dry method, electric current measuring method, neutron-applying method, and the microwave-irradiating method mentioned above. When measuring the water content by irradiating microwave, since the objective sample is directly set inside of a waveguide, some particles of the sample adhere to the inner wall of the waveguide as residue to eventually cause error to occur in the course of rating the water content of sample of other material in the following test. Furthermore, when directly inserting sample into the waveguide, since the sample may be leant to any one or two sides of the waveguide, it is difficult for the operator to uniformly set the sample in the waveguide, and thus, the resulting error also occurs.

The object of the invention is to fully solve those problems mentioned above present in any of conventional water-content determining apparatuses by irradiating a microwave to a sample of powder/granule material using a novel apparatus which is capable of easily and precisely measuring water content of powder/granule sample.

SUMMARY OF THE INVENTION

To achieve the above object, the apparatus for determining water content of powder/granule sample in accordance with the invention is provided with a rectangular waveguide system which is substantially set up in the upright or vertical disposition, and which has a microwave transmitting converter, a microwave waveguide, and a microwave receiving converter; the apparatus comprising:

a sample container which contains powder or granular sample and is accommodated inside of the microwave waveguide;

said waveguide being provided with an inlet hole communicated to the inner space of said waveguide system at a side wall and also being provided with a door for opening and closing said hole and means for supporting said sample container within said waveguide;

a buffer weighing system for supporting said waveguide system on a supporting table in the upright or vertical disposition and generates electric signals designating the supported weight; and signal processing means for receiving signal output from said microwave receiving converter and the other signal from said buffer weighing system, storing and arithmetically processing these signals whereby said signal processing means computes water content of sample based on the ratio value sought from the one calculated by subtraction of the weight output of said waveguide system at the time of accommodating the empty container from the weight output of said waveguide system when fully loading sample inside of the container, against the amount of microwave absorbed by said sample calculated by subtration of the microwave output while accommodating the sample-loaded container in the waveguide from the microwave output while accommodating the empty container.

When operating any conventional microwave-irradiation type, powder/granule water-content measuring apparatus, precision of the measurement lowers because of the uneven distribution of the density of sample loaded inside of the waveguide, in particular, by the unevenness of the sample in the cross section of the waveguide. As a matter of course, precision of the measurement is lowered by the leant disposition of sample in the cross section of the waveguide. As the secondary cause, precision in the measurement of water content is also lowered by presence of residual sample which dispersedly adheres to the inner wall of the waveguide. This is because the residual sample interferes with the ensuing water-content measuring operations and causes error to take place. Furthermore, if the sample particles infiltrate into the coupling elements at both ends of the waveguide and then disturb the impedance matching of impedance of the waveguide to the energy source portion, and to the measurement portion, then, the precision in the measurement of water content also lowers. The water-content measuring apparatus according to the invention provides a portable sample container so that the objective sample can fully be loaded by way of uniform density by giving a vibration to it. The operator can set sample to the inner space of the waveguide in the uniform density merely by disposing the sample-filled container inside of the waveguide, and thus, the water-content measuring apparatus of the invention finally prevents the lowering of the precision in the measurement caused by uneven density of the loaded sample. Since the sample can evenly be disposed merely by setting the sample-filled container to the inner space of the waveguide, the apparatus embodied by the invention securely prevents the lowering of precision in the measuring operation otherwise caused by the infiltration of sample particles into the inner structure of the waveguide and also by the adhesion and infiltration of residual sample to the inner wall and into the coupling elements on both sides of the waveguide.

If only the operator carefully handles the container filled with sample, the sample particles rarely spills off from the container and enters into the coupling elements of the waveguide (particularly into the signal receiving element in the bottom part). However, the apparatus of the invention perfectly prevents sample particles from penetrating into the coupling elements of the waveguide even when the sample particles spill out of the container merely by providing such a supporting plastic plate which can physically shield the bottom connection elements and has sufficient microwave permeability.

Furthermore, since the apparatus uses a portable container for loading sample so that the operator can easily insert and take the sample-filled container into and out of the waveguide. This allows the operator to easily and properly set the sample. Furthermore, since there is no fear of staining the interior of the waveguide will spill particles of sample, operator can easily clean the interior of the waveguide, thus significantly promoting the efficiency in the measurement of water content.

DESCRIPTION OF THE EMBODIMENTS

Figure 1:
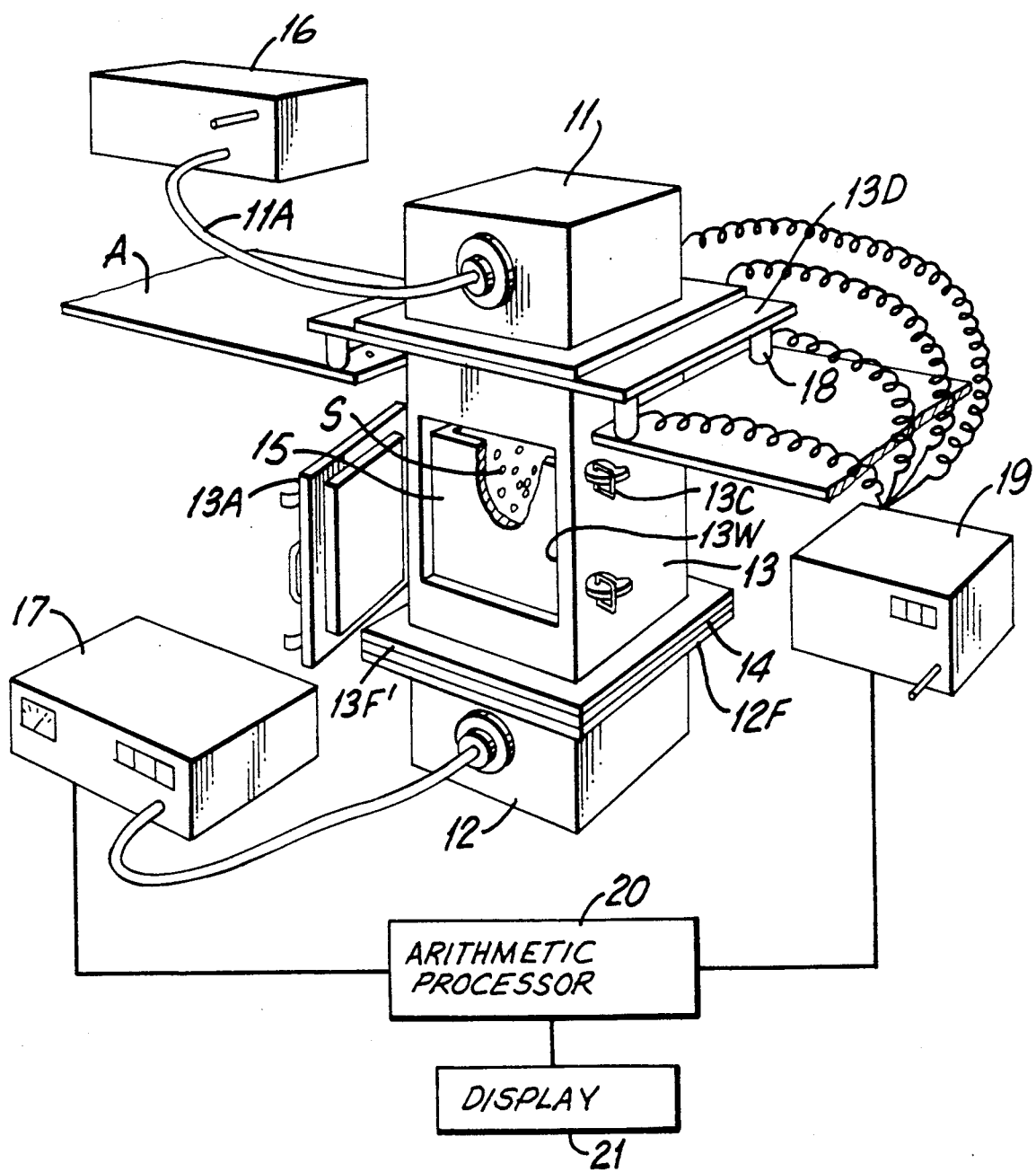
FIG. 1 is a perspective view of the water-content measuring apparatus representing an embodiment of the invention with a simplified block diagram illustrating the electric connection of arithmetic processing/display means.

FIG. 1 shows a typical embodiment of the water-content measuring apparatus according to the invention. FIG. 1 designates the waveguide system making up the main unit of the system, which is substantially uprightly disposed. A microwave transmitting coaxial waveguide converter 11 at the top portion of the unit makes the matching of impedance between a coaxial cable 11A available for feeding microwave and a waveguide 13. A microwave receiving coaxial waveguide converter 12 makes the matching of impedance between the coaxial cable 11A and the waveguide 13. The microwave transmitting coaxial waveguide converter 11 and the microwave receiving coaxial waveguide converter 12 each having substantially identical section are respectively connected to the upper and lower ends of the waveguide 13 having the rectangular section. A supporting plate 14 made from plastic material is inserted between flanges 12F and 13F' of the microwave receiving coaxial waveguide converter 12 and the waveguide 13. An inlet hole 13W is provided for the front surface as of the four side surfaces of the waveguide 13. The closing door 13A is secured to the edge of this surface by means of hinge connection so that the operator can put the container 15 filled with sample S into and out of the waveguide system through the inlet hole 13W. The plastic container 15 has an opening on the upper surface and the horisontal section which fits the inner surface of the waveguide 13. The door 13W is held to the closed position for the hole 13W of the waveguide 13 by means of hook-lever latch 13C to tightly seal the interior of the waveguide 13.

Figure 2:
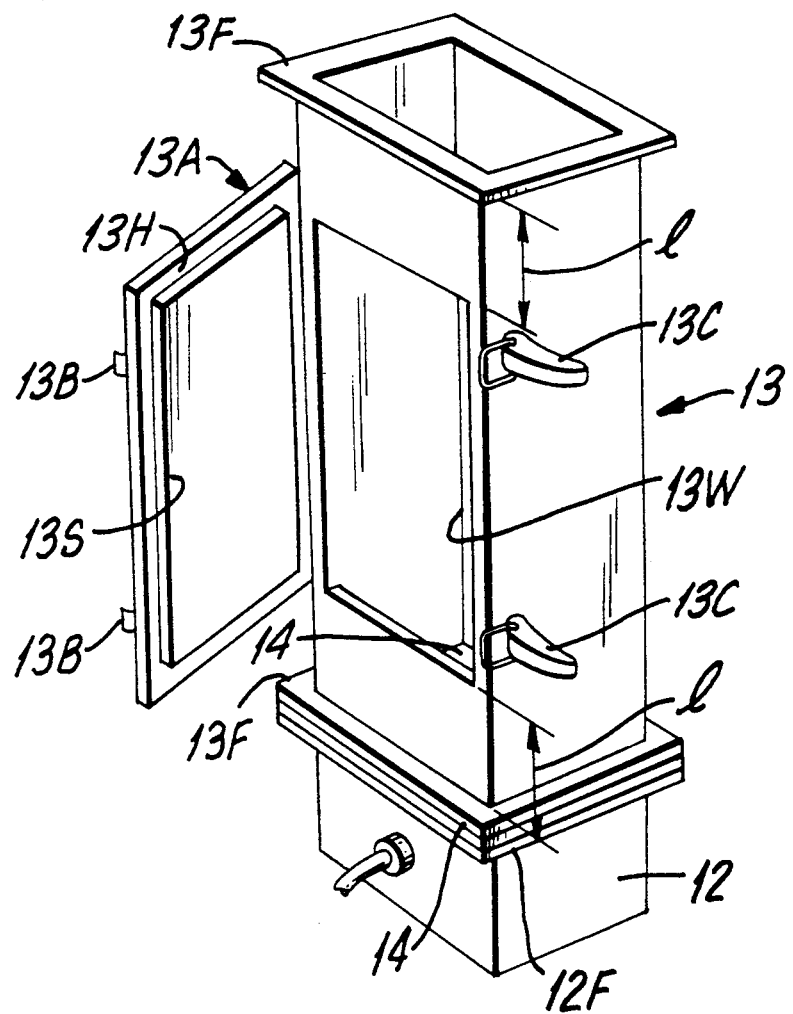
FIG. 2 is a perspective view representing the detail of the inlet hole on a side surface of the waveguide.

As is expressly shown in FIG. 2, the hole 13W on the front surface of the waveguide 13 has a specific width identical to the waveguide 13, while the upper and lower ends of the hole 13W are respectively apart from the upper and lower flanges 13F and 13F' across the length "l". The door 13A is internally provided with a flat hill or step member 13S fitting the periphery of the hole 13W so that the surface of the step member 13S can become flush with the front inner surface of the waveguide 13 when the door 13A is fully closed. In the closed position of the door 13A, the outwardly protruded member 13H surrounding the step member 13S comes into contact with the front external surface of the waveguide to shield the clearance between the periphery of the hole 13W of the waveguide 13 and the periphery of the step member 13S of the door 13A so that a high-frequency energy can be prevented from leaking outside through the clearance. The clearance does not obstruct the flow of electric current along the inner surface of the waveguide 13.

Even if the sample particles S are accidentally scattered to the inner surface of the waveguide 13 from the container 15, the plastic plate 14 effectively prevents the scattered particles from infiltrating into the microwave receiving coaxial waveguide converter 12 and adhering to the internal elements. After being placed inside of the waveguide 13, the sample-filled container 15 is mounted on the plastic plate 14. The microwave oscillator 16 feeds a microwave energy to the microwave transmitting coaxial waveguide converter 11 via a coaxial cable. The power meter 17 is connected to the microwave receiving coaxial waveguide converter 12 via another coaxial cable. On receipt of the microwave, the power meter 17 detects the intensity of the received microwave. A total of four units of load cells 18 as a buffer weighing system are set to four corners of the bottom surface of the flange 13D which protrudes itself from the upper end of the side surfaces of the waveguide 13. The whole structure of the waveguide system is mounted on the upper surface of the supporting base A via the load cells 18. The total weight of the entire apparatus including the waveguide 13, the upper and lower converters 11 and 12, and those components accommodated inside of waveguide 13, is converted into electric signals by each load cell 18 according to the amount shared by each of these four load cells 18. Each of the weighed value shared by four load cells 18 is then summed up by the weighing instrument 19, which then outputs the summed-value signal designating the total weight. The arithmetic processor 20 receives and stores microwaves output from the power meter 17 at the time of placing the sample-filled container 15 inside of the waveguide 13 and at the time of placing the empty container 15 inside of the waveguide 13. The arithmetic processor 20 calculates the difference between the received microwave at the time of placing the empty container 15 and the other received microwave at the time of placing the sample-filled container 15, i.e., it calculates the amount of microwave absorbed by sample. Then, the arithmetic processor 20 calculates the net weight of sample S from the difference between the sample-set weight and the sample-free weight delivered from the weighing instrument 19, and then, based on those calculated results, the arithmetic processor 20 calculates the water content of sample S from the net weight of sample S and the amount of microwave absorbed by sample S or the attenuated amount of microwave prior to finally allowing display 21 to indicate the water content together with a variety of data or the parameter used for the measuring operation.

Next, the steps of calculating the water content $\phi$ from the attenuated amount of microwave $\Delta V$ is described below.

Assume that the intensity of the microwave-detected output signal before loading the sample S into the waveguide 13 is Vi and the intensity of the microwave-detected output signal after loading the sample S into the waveguide 13 is Vs, then, the attenuated amount of microwave can be calculated by applying the equation $\Delta V = Vi - Vs$. Furthermore, assume that the net weight of the sample is Ws and the volume of water in the sample is Wh, then, the water content $\phi$ can be defined by applying the equation shown below.

$$\phi = (Wh/Ws) \times 100 (\%) \tag{1}$$

Assume the attenuated amount of microwave $\Delta V$, must relate to the net weight of the sample Ws and the volume of water in the sample Wh.

Furthermore, if A, B and C respectively represents the test constants in dealing with $\Delta V$ ($\mu W$), Wh (kg), and Ws (kg), the following equation can be set.

$$\Delta V = A + BWh + CWs \quad (2)$$

Rearranging equation (2):

$$Wh = (\Delta V - A - CWs)/B \quad (2')$$

As a result, the water content $\phi$ can be calculated by applying the equation shown below. Substituting equation (2') into equation (1), resulting in the elimination of Wh, thus forming:

$$\phi = \frac{\Delta V - A - CWs}{BWs} \times 100 \ (\%) \quad (3)$$

or $$\phi = \frac{\Delta V - A}{BWs} \times 100 - C' \ (\%) \quad (4)$$

where $C' = C/B \times 100$.

In this example, a variety of chips (a total of 22 kinds of chips including hard wood and mangrove) were used for composing the sample. To implement a variety of tests, the inventors used 1 GHz of the microwave frequency. As described in the above, the inventors used kilogram to express the weight unit, and W to express the unit of the attenuated amount of microwave. As a result of the tests, the inventors obtains the values of constants A, B and C to be A = -0.809, B = 1.447, C = 3,551, and C' = 254.4, respectively. Based on the data of the water content $\phi$ calculated from the above equations, the inventors computed the correlation coefficient $\phi/\phi_o = \gamma$ (where $\phi_o$ equals water content of same sample S measured by absolute dry method) and finally achieved $\gamma = 0.99$. It is apparent from this result that the apparatus embodied in accordance with the invention can measure the water content with extreme accuracy.

As mentioned earlier, if the water-content measuring operations were repeatedly carried out without using the sample-shielding plate, fine particles of sample easily infiltrate into the coaxial waveguide coupling elements to vary the impedance and also vary the input level of microwave or the microwave-detected output signal. The plastic plate 14 effectively prevents these undesired problems from occurrence. As is quite necessary for the container 15, it is also essential for the system to properly select such a useful plastic plate featuring the minimum rate of absorbing and attenuating the microwave, the minimum dielectric constant and dielectric loss, and the minimum rate of water absorption. To fully satisfy these requisites, it is suggested to use any of those plastic plates made from polypropylene, or polyester, or polyoxymethylene, or a variety of polymers, or copolymers like ABS, or the one made from ceramic, for example. Care should be taken to properly select the thickness of the plastic plate. Excessive thickness of the plastic plate gravely affects the microwave output and the microwave-detected output signal.

When loading the sample into the container 15, it is essential for the operator to mechanically oscillate in an appropriate manner the container during and/or immediately after completing the sample loading operation so that the sample can be loaded and distributed inside of the container with a uniform density. Also, care should be taken to prevent the sample content from being leant on one side when setting the sample-filled container 15 inside of the waveguide 13.

There are a variety of objects that can be measured by the water-content measuring apparatus in accordance with the invention including the concrete/raw-material mixture, tobacco leaves, gravel, wood chip, dry confectionary like cookies, cotton, and a variety of powder and granules like cereals, for example.

The waveguide 13 may be of rectangular or cylindrical shape. The plastic container 15 may not always be of the sealing type, but it may have an opening on the top surface provided that the loaded sample cannot spill outside of the container 15 by maintaining the opening at the uppermost position of it as shown in FIG. 1.

According to the invention, the operator can easily set the sample-filled container into the waveguide. This prevents sample from scattering or remaining inside of the waveguide and allows the operator to easily handle the sample. Since the embodiment of the apparatus in accordance with invention allows the sample to be loaded into the waveguide with a uniform density distribution without being leant, the accuracy of the water-content measuring is significantly improved. Furthermore, since there is no fear of staining the interior of the waveguide with spilled or scattered particles of the sample, operator is free from the need of cleaning the interior of the waveguide in each cycle of the measuring operation.

Since the sample-setting operation can easily be done merely by loading sample into the container and then setting the sample-filled container inside of the waveguide, the efficiency in the measurement of water content is greatly promoted, and yet, the operator can conveniently handle the sample-filled container.

What we claimed is:

1. An apparatus for determining water content of powder/granule sample including a rectangular waveguide system substantially set up in the upright or vertical disposition, consisting of a microwave transmitting converter, a microwave waveguide, and a microwave receiving converter, the apparatus comprising:

a sample container for containing powder or granular sample and being accommodated inside of the microwave waveguide;

said waveguide being provided with an inlet hole communicated to an inner space of said waveguide system at one of side walls, and having a door for opening and closing said hole and means for supporting said sample container within said waveguide;

a buffer weighing system for supporting a hollow waveguide on a supporting table in the upright or vertical disposition and generates electric signals designating a supported weight; and signal processing means for receiving signal output from said microwave receiving converter and from said buffer weighing system, storing and arithmetically processing these signals whereby said signal processing means computes water content of sample container.

2. The apparatus according to claim 1, wherein said sample container is made from a water repellent plastic material prossessing a low complex dielectric content and low attenuation characteristic for microwaves, and a high degree of electrical insulation.

3. The apparatus according to claim 2, wherein said sample supporting means is a plate for closing a lower end of said waveguide, said plate made from the same material as the material of said container.

4. The apparatus according to claim 1, wherein the signal processing means computes the % water content of the sample by the equation:

$$\frac{(V_i - V_s) - A}{BW_s} \times 100 = C$$

whereby:

$V_i$ = intensity of the microwave output when accommodating the empty container.

$V_s$ = intensity of the microwave output while accommodating the sample-loaded container.

A, B and C = test constants $W_s$ = net weight of the sample and $C^1 = C/B \times 100$.

5. The apparatus according to claim 1, wherein the door has a step member in an inner surface of the door fitting the periphery of the hole so that a surface of the step member is flushed with the inner surface when the door is closed, the door is held closed by a latch means to tightly seal the door.

6. The apparatus according to claim 1 wherein the hole has a specific width identical to that of a resonator of a waveguide.

7. The apparatus according to claim 4, wherein the door has a step member in an inner surface of the door fitting the periphery of the hole so that a surface of the step member is flushed with the inner surface when the door is closed, the door is held closed by a latch means to tightly seal the door.

8. The apparatus according to claim 4, wherein the hole has a specific width identical to that of a resonator of a waveguide.

9. The apparatus according to claim 4, wherein said sample container is made from a water repellant plastic material possessing a low complex dielectric content and low attenuation characteristic for microwaves, and a high degree of electrical insulation.

10. The apparatus according to claim 4, wherein said sample supporting means is a plate for closing a lower end of said waveguide, said plate made from the same material as the material of said container.

* * * * *